United States Patent [19]

Haslam et al.

[11] Patent Number: 4,530,928

[45] Date of Patent: Jul. 23, 1985

[54] QUINOLINE CARBOXYLIC ACID COMPLEXES WITH GUANIDINIUM CARBONATE

[75] Inventors: John L. Haslam; Stefano A. Pogany, both of Lawrence, Kans.

[73] Assignee: Merck & Co., Inc., Rahway, N.J.

[21] Appl. No.: 451,314

[22] Filed: Dec. 22, 1982

Related U.S. Application Data

[63] Continuation-in-part of Ser. No. 339,039, Jan. 13, 1982, abandoned.

[51] Int. Cl.³ .................. A61K 31/495; C07D 401/02
[52] U.S. Cl. ..................................... 514/254; 544/383
[58] Field of Search ........................ 544/363; 424/250

[56] References Cited

U.S. PATENT DOCUMENTS

| | | | |
|---|---|---|---|
| 4,255,424 | 3/1981 | Hannah | 544/263 |
| 4,292,317 | 9/1981 | Pesson | 544/363 |

FOREIGN PATENT DOCUMENTS

| | | | |
|---|---|---|---|
| 2939786 | 4/1980 | Fed. Rep. of Germany | 544/363 |
| 0004974 | 1/1982 | Japan | 544/363 |
| 0176961 | 10/1982 | Japan | 544/363 |

OTHER PUBLICATIONS

Stenger, et al., "Chemical Abstracts", vol. 80, 1974, col. 27258d.
Haslam, et al., "Chemical Abstracts", vol. 99, 1983, col. 99:181462q.

*Primary Examiner*—Glennon H. Hollrah
*Assistant Examiner*—James H. Turnipseed
*Attorney, Agent, or Firm*—Mario A. Monaco; Manfred Polk; Michael C. Sudol, Jr.

[57] ABSTRACT

This invention involves complexes of quinoline carboxylic acid derivatives with guanidine and guanidine carbonate. The complexes have a greater solubility and dissolution rate when compared to the parent quinoline carboxylic acid derivatives and thus are more effective anti bacterials than the parent acids.

9 Claims, No Drawings

QUINOLINE CARBOXYLIC ACID COMPLEXES WITH GUANIDINIUM CARBONATE

RELATED APPLICATIONS

This case is a continuation-in-part of our previous parent case, U.S. Ser. No. 339,039, now abandoned, filed in the United States Patent and Trademark Office on Jan. 13, 1982.

BACKGROUND OF THE INVENTION

Certain quinoline carboxylic acid derivatives are known in the art as having anti-bacterial activity. In particular a quinoline carboxylic acid specifically defined as 1-ethyl-6-fluoro-1,4-dihydro-4-oxo-7-(1-piperazinyl)-3-quinoline carboxylic acid is known in the art as an anti-bacterial agent and is known particularly as AM-715 a new nalidixic acid analog. This particular compound is described in "Anti-Microbial Agents and Chemotherapy", February 1980, page 103 to 108, Volume 17, No. 2. In that article the compound AM-715 is described as having a broad spectrum of anti-bacterial activity against gram-positive and gram-negative bacteria, and that the anti-bacterial activity of AM-715 was greater than those of pipemidic acid and nalidixic acid. AM-715 has very low water solubility at the most normally used pH range of 6–10. Also it is very soluble in acetic acid but rather insoluble in solvents such as acetone, ethanol benzene or ethyl ether, and it has a rather slow rate of dissolution. Thus it is imperative in this field to discover a pharmaceutically effective derivative of quinoline carboxylic acid which is a better solubilized compound to allow more quinoline carboxylic acid compound to be introduced into the blood stream of a human to counteract bacterial infections which this particular compound is good against.

SUMMARY OF THE INVENTION

It has been discovered that when quinoline carboxylic acid derivatives of the formula

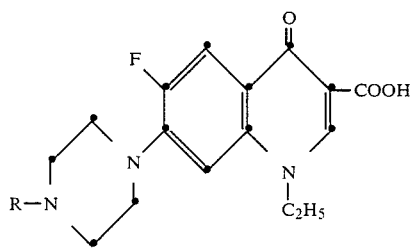

wherein R is H or alkyl having from 1–6 carbon atoms such as methyl, ethyl, isopropyl, pentyl but particularly methyl are reacted with guanidinium carbonate, complexes of the quinoline carboxylic acid with guanidine and guanidinium carbonate are formed. The two complexes have the following formulae:

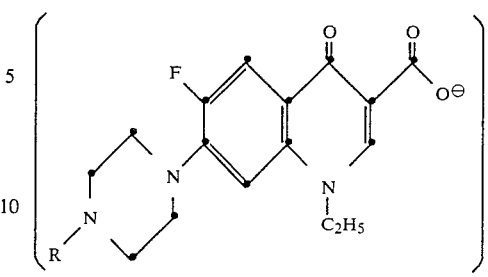

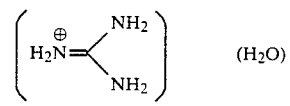

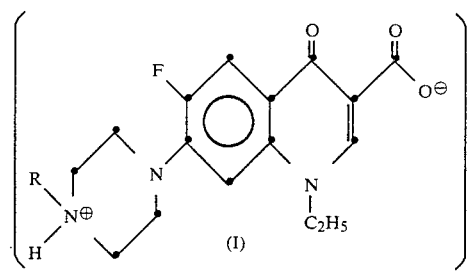

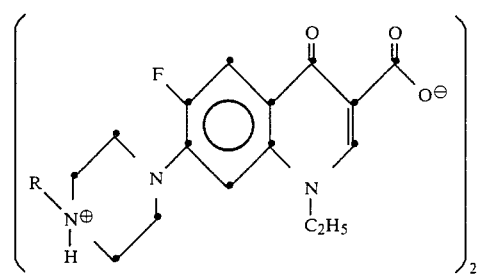

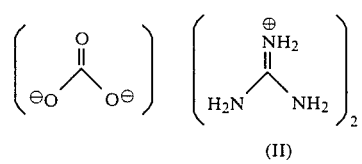

wherein R is as previously defined.

Preferred complexes are those wherein R is hydrogen and still more preferred are those complexes of formula II. It has been found that complexes (I) and (II) have increased water solubility over the quinoline carboxylic acid derivative itself and also have a greater rate of dissolution than the parent compound thereby altering the biopharmaceutics of the compound.

Complexes I and II are antibacterial agents and have activity against gram positive and gram negative bacteria.

The compounds of this invention can be administed in a wide variety of therapeutic dosages in conventional vehicles as, for example, by oral administration in the form of a tablet or by intravenous injection. Also, the daily dosage of the products may range from 100 mg to 1600 mg. of the active ingredient for the symptomatic adjustment of the dosage to the human patient to be treated. These dosages are well below the toxic or lethal dose of the products.

The methods of administration to a human patient suffering from bacterial infections and in need of treatment of such infections can vary. The route of oral administration is the most preferred one. Specifically, the complex (Formula I or II or both) should be placed into an enteric coated capsule which will remain intact in the acidic environment of the stomach.

When the capsule exits from the stomach it will encounter the alkaline environment of the gut and it will dissolve, releasing the complex. The complex will at this point be absorbed through the gut-wall by virtue of its increased water solubility over the non-complexed quinoline carboxylic acid. The second most preferred method of administration is by the rectal route, in other words, via a suppository. The third preferred route of administration is by intravenous injection.

A suitable unit dosage form of the products of this invention can be administered by mixing 50 milligrams of complexes (I) or (II) with 149 mg. of lactose and 1 mg. of magnesium and placing the 200 mg. mixture into a No. 1 gelatin capsule. Similarly, by employing more of the active complex and less lactose, other dosage forms can be put up in No. 1 gelatin capsules and should it be necessary to mix more than 200 mg. of ingredients together, larger capsules may be employed. Compressed tablets, pills, enteric coated tablets or capsules, or other desired unit dosages can be prepared to incorporate the compounds of this invention by conventional methods, and, if desired, can be made up as injectable solutions by methods well known to pharmacists. An effective amount of the drug is ordinarily supplied at a dosage level of from about 0.1 mg to about 50 mg./kg. of body weight. Preferably the range is from about 1 mg to 7 mg./kg. of body weight.

Another route of administration is the ophthalmic one for the treatment of ocular infections.

This is accomplished by instilling in the eye a conventional ophthalmic suspension containing for instance from 0.1 to 0.5% of the complex (Formulae I and II) in a viscosity involving agent.

The ophthalmic suspension of the complexes of this patent have the advantage over the non-complexed antibiotic, in that they provide higher concentrations for longer times without producing precipitation of the drug in the eye.

Complexes I and II of the quinoline carboxylic acid derivatives can be prepared by reacting the quinoline carboxylic acid derivative with guanidinium carbonate by dissolving said quinoline carboxylic acid derivative and guanidinium carbonate in water and heating.

Complex I can be prepared by dissolving one equivalent of the quinoline carboxylic acid with approximately 0.7 equivalents of guanidinium carbonate, wherein Complex II can be formed by combining 1 equivalent of quinoline carboxylic acid with approximately two equivalents of guanidinium carbonate.

To prepare either complex, the mixture can be heated at a temperature of from 60° C. to 100° C. for a time sufficient to dissolve the quinoline carboxylic acid derivative. Once the reaction is complete the desired complex I or II can be removed from the reaction mixture by known methods in the art such as for example by filtering off the desired crystals and drying said finished product.

Our invention can be illustrated by the following examples. These examples should merely be taken as illustrations of the invention and not limitations thereof.

EXAMPLE 1

Preparation of the guanidine cabonate complex with 1-ethyl-6-fluoro-1,4-dihydro-4-oxo-7-(1-piperazinyl)-3-quinoline carboxylic acid Complex of Formula II 1-Ethyl-6-fluoro-1,4-dihydro-4-oxo-7-(1-piperazinyl)-3-quinoline carboxylic acid (1 g, 3.13 mmol) and guanidinium carbonate (1.13 g, 6.26 mmol) were dissolved in 20 mL of distilled water by heating. The slightly yellow solution was allowed to cool to room temperature. The diamond-shaped crystals of the complex began to form in approximately 2 hours and the crystallization process was allowed to proceed without disturbing it for 24 hours. The crystals were isolated by suction filtration and were dried at 78° C. for several hours. The IR spectrum (KBr pellet) shows complete disappearance of the peak at 1720 cm$^{-1}$ and shows prominent peaks at 3400–2800, 1670, 1610, 1570 and 1490 cm$^{-1}$. The elemental analysis fits correctly a molecular complex made of 2 molecules of the parent quinoline carboxylic acid and 1 molecule of guanidinium carbonate. Anal.-Calc. for $C_{35}H_{48}N_{12}O_9F_2$: C, 51.34; H, 5.9; N, 20.52. Found: C, 51.51; H, 6.21; N, 20.68.

EXAMPLE 2

Preparation of the guanidine complex with 1-ethyl-6-fluoro-1,4-dihydro-4-oxo-7-(1-piperazinyl)-3-quinoline carboxylic acid Complex of Formula I 1-Ethyl-6-fluoro-1,4-dihydro-4-oxo-7-(1-piperazinyl)-3-quinoline carboxylic acid (e.g., 3.13 mmol) and guanidinium carbonate (0.4 g, 2.21 mmol) were dissolved in 20 ml of water by heating. The solution was allowed to cool at 25° C. The rectangular crystals of the complex began to form in about 1 hour and the crystallization process was not disturbed for 24 hours. The crystals were isolated by suction filtration and were dried at 28° C. in vacuum for 12 hours. The IR spectrum (KB$_2$ pellet) shows complete disappearance of the peak at 1720 cm$^{-1}$ and shows prominent peaks at 3500–2800, 1660, 1610, 1570 and 1490 cm$^{-1}$. The elemental analysis fits correctly the desired product. Anal. Calc. for $C_{33}H_{43}N_9O_7F_2$: C, 55.37; H, 6.05; N, 17.61. Found: C, 55.24; H, 6.28; N, 17.60.

EXAMPLE 3

Solubility of the complex in water

The solubility of complex of Example 1 at 25° C. in water is 12.5 mg/mL which is equivalent to a solubility of 1-ethyl-6-fluoro-1,4-dihydro-4-oxo-7-(1-piperazinyl)-3-quinoline carboxylic acid (parent compound) in water of 9.8 mg/mL. Since the reported water solubility of the parent compound is 0.2 mg/mL, the ratio 9.8/0.2=49 shows that solubility has been improved 49 times.

Table I provides additional solubility data fo the complex of Example 1 at 37° C. and solubility values for complex of Example 2 at 25° and 37° C.

TABLE I

Solubility in Water of 1-ethyl-6-fluoro-1,4-dihydro-4-oxo-7-(1-piperazinyl)-3-quinoine carboxylic acid (parent) and its complexes (Example 2) and (Example 1)

| Compound | Temperature °C. | Solubility mg/ml | m Molar | Equivalent Solubility as parent mg/ml | m Molar |
|---|---|---|---|---|---|
| Parent | 25 | 0.20 | 0.63 | 0.20 | 0.63 |
| Complex (Example 2) | 25 | 6.6 | 9.1 | 5.8 | 18.2 |
|  | 37 | 8.5 | 11.9 | 7.6 | 23.8 |
| Complex (Example 1) | 25 | 12.5 | 15.3 | 9.8 | 30.6 |
|  | 37 | 17.6 | 21.5 | 13.7 | 43.0 |

What is claimed is:

1. A guanidino carbonate or guanidino complex having the formula

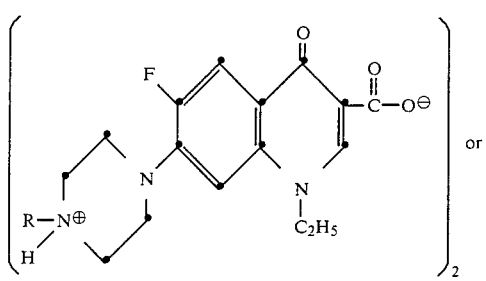

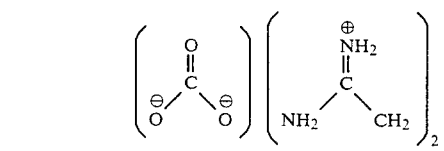

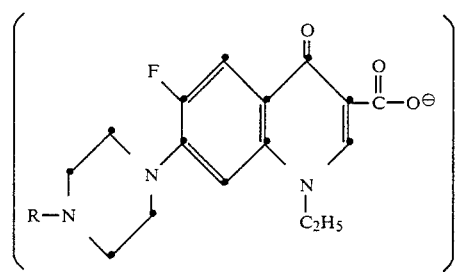

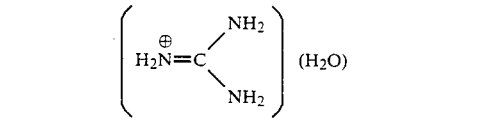

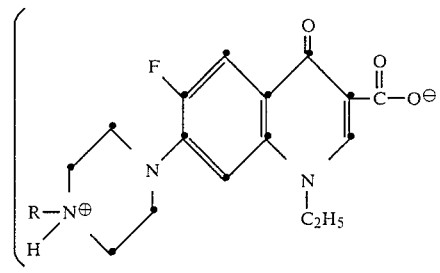

wherein R is hydrogen or $C_{1-6}$ alkyl.

2. The complexes of claim 1 wherein R is hydrogen.

3. The guanidinium carbonate complex of 1-ethyl-6-fluoro-1,4-dihydro-4-oxo-7-(1-piperazinyl)-3-quinoline carboxylic acid.

4. A method of treating a patient suffering from bacteria infection which comprises administering a therapeutically effective amount of a composition comprising a guanidino carbonate or guanidino complex of the formula:

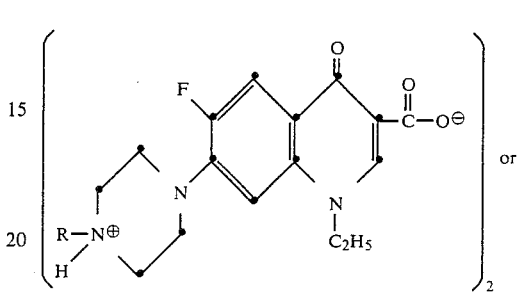

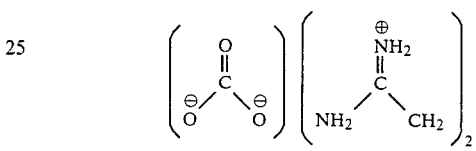

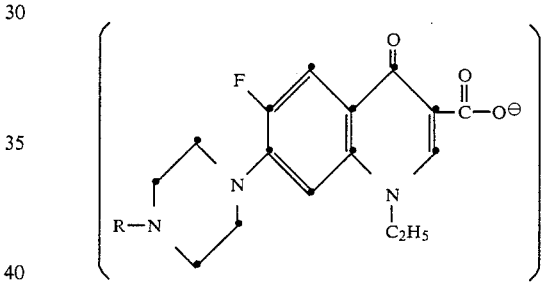

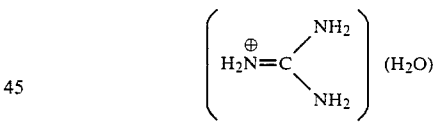

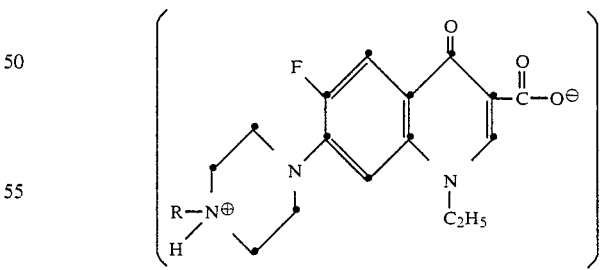

wherein R is hydrogen or $C_{1-6}$ alkyl.

5. A method of treatment according to claim 4 wherein R is hydrogen.

6. A method of treating infection caused by bacteria by administering to a patient suffering from such infections a therapeutically effective amount of a composition comprising the guanidinium carbonate complex of 1-ethyl-6-fluoro-1,4-dihydro-4-oxo-7-(1-piperazinyl)-3-quinoline carboxylic acid.

7. An antibacterial pharmaceutical composition comprising as an active ingredient the guanidino carbonate or guanidino complex of the formula:

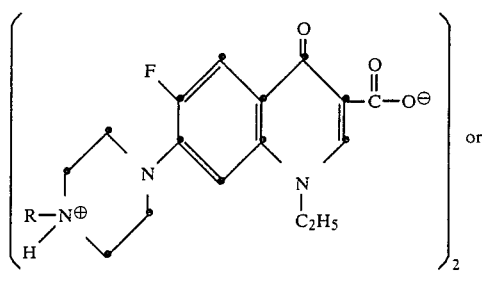 or

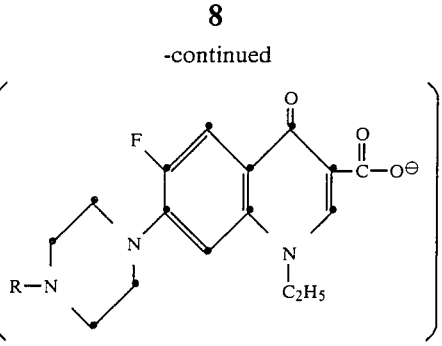

wherein R is hydrogen or $C_{1-6}$ alkyl and a pharmaceutically acceptable carrier.

8. The pharmaceutical composition of claim 7 wherein R is hydrogen.

9. An antibacterial composition comprising as an active ingredient the guanidinium carbonate complex of 1-ethyl-6-fluoro-1,4-dihydro-4-oxo-7-(1-piperazinyl)-3-quinoline carboxylic acid.

* * * * *